United States Patent [19]

Enright

[11] Plant 4,750

[45] Jun. 30, 1981

[54] GAZANIA PLANT

[76] Inventor: Paul C. Enright, 11615 Riverside Dr., Lakeside, Calif. 92040

[21] Appl. No.: 150,603

[22] Filed: May 16, 1980

[51] Int. Cl.[3] ..... A01H 5/00

[52] U.S. Cl. ..... Plt./68

[58] Field of Search ..... Plt./68

*Primary Examiner*—Robert E. Bagwill

[57] ABSTRACT

A novel Gazania seedling distinguished by its two distinctly different leaf patterns and distinctively rayed flowers. Petals are patterned with basal rings of, first, Gargoyle, followed by a second ring of Ivy Green. On elongated central stripe of Zanzibar extends from the second ring and fades progressively toward the tip into Cadnium Yellow which defines substantially the entire petal margin.

1 Drawing Figure

The present invention relates to a new and distinct variety of Gazania plant, which I choose to name Royal Tiger. This new and distinct variety of Gazania plant is characterized by its unique flower and varying leaf shapes.

The new variety was discovered as a seedling at my growing grounds, located in Lakeside, Calif., in a cultivated row of Super Fiesta Gazania (an unpatented new variety which has an orange flower with black and orange rayed stripes).

Asexual reproduction of the new variety has been accomplished by taking cuttings. Numerous cuttings have been made at my Lakeside, Calif. growing grounds and all of the resulting plants have exhibited the above-mentioned distinguishing characteristics which have been transmitted through succeeding propagations, thereby establishing that the strain is true.

The accompanying photographs in full color show the flower and foliage of the new and distinct variety of Gazania plant. These color photographs are as correct as it is possible to reproduce thecolor of the flower and foliage.

A detailed description of the new and distinct variety follows. To facilitate identification of the important colors referred to in this specification, the color terminology adopted by the *Dictionary of Color* by Maerz and Paul has been adopted.

THE PLANT

Form: Ground cover type plant that is best described as trailing.

Foliage:

*Quantity.*—Abundant.

*Shape.*—There are two distinct shapes of leaves. Both leaves have a 2"-2½" linear base. The tip of one type is oblanceolate with apex acute, whereas the other type is parted near the tip with 2-5 partitions.

*Size.*—Full grown leaves are 5"-6½" in length with the oblanceolate-acute shaped leaves varying from 5/16"-⅜" at the widest portion, and the parted shaped leaves varying from ⅞"-1⅛" at the widest portion.

*Ribs and veins.*—The veins are not prominent on either side of the leaf, while the central rib is very prominent on the underside of the leaf, and terminates at the apex as a sharp line.

*Texture.*—The leaves are thick and have a sericeous covering top and bottom.

*Color.13* The upper side of the leaf is Aspen Green$^T$ plate 31/C6. The under side of the leaf is dull White plate 9/A1, with the central rib being a dull Green plate 22/H4.

*Leaf margins.*—Half of the leaves have margins that are entire, and the other half are parted near the tip.

THE FLOWER

Blooming habit: The new variety seems to bloom throughout the year in Southern California.

Buds:

*Size.*—Most buds are from 9/16"-⅝" in diameter.

*Form.*—Buds are campanulate in shape, from whicha pointed tip emerges.

Flower:

*Size.*—The size of the bloom varies from 2"-2⅜" in diameter.

*Form.*—The overall flower shape is round and flattened, with the petals being ligulate in shape. A typical flower has 21 petals.

*Borne.*—Flowers are borne singly on a stem that can be up to 9½" in length.

*Color.*—The flower is bright Cadnium Yellow$^P$ plate 9/L8 with Zanzibar$^T$ plate 8/L5 rayed stripes which start at the base of the petals and fade to Cadnium Yellow$^P$ as they approach the tip. The flower has two basal rings; the inner ring is Gargoyle$^T$ plate 16/C1 and the outer ring is Ivy Green plate 16/L9. As the flower ages, its original color fades.

*Petal shape.*—The petals are attenuate-obtuse in shape and curl to an acuminate-like tip with age. The petals are 1"-1⅜" in length and are about ⅜" at the widest portion.

I claim:

1. A new and distinct variety of Gazania plant substantially as herein described, characterized particularly as to novelty by its unique flower and varying leaf form.

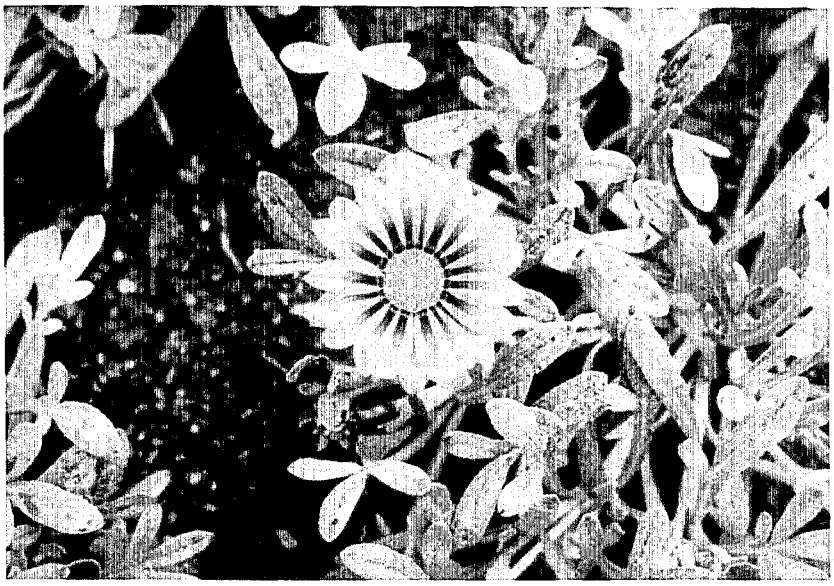

* * * * *